United States Patent [19]

Moore, Jr.

[11] Patent Number: 4,612,368

[45] Date of Patent: Sep. 16, 1986

[54] PROCESS FOR PREPARING 2,2'-AZOBIS(2-METHYLBUTANENITRILE)

[75] Inventor: Earl P. Moore, Jr., Wilmington, Del.

[73] Assignee: E. I. Du Pont de Nemours and Company, Wilmington, Del.

[21] Appl. No.: 272,580

[22] Filed: Jun. 3, 1981

[51] Int. Cl.⁴ .................... C07C 107/02; C08F 2/04; C08F 2/24; C08F 2/28

[52] U.S. Cl. .................................. 534/578; 534/587

[58] Field of Search ................. 260/192; 534/578, 587

[56] References Cited

U.S. PATENT DOCUMENTS

| | | | |
|---|---|---|---|
| 2,711,405 | 6/1955 | Anderson | 260/192 |
| 3,783,148 | 1/1974 | Fuchs | 260/192 |
| 3,937,696 | 2/1976 | Knowles et al. | 260/192 |
| 3,987,025 | 10/1976 | Moore | 260/192 |
| 4,028,345 | 6/1977 | Moore | 260/192 |
| 4,039,527 | 8/1977 | Nagaoka et al. | 260/192 |
| 4,051,124 | 9/1977 | Moore | 260/192 |
| 4,061,590 | 12/1977 | Moore | 260/192 |
| 4,132,729 | 1/1979 | Moore | 260/192 |
| 4,218,371 | 8/1980 | Moore | 260/192 |
| 4,272,435 | 6/1981 | Matsuda et al. | 260/192 |

FOREIGN PATENT DOCUMENTS

| | | | |
|---|---|---|---|
| 2849370 | 5/1979 | Fed. Rep. of Germany | 534/578 |
| 2007657 | 5/1979 | United Kingdom | 534/578 |

Primary Examiner—Floyd D. Higel

[57] ABSTRACT

A process for the preparation of 2,2'-azobis(2-methylbutanenitrile) in high yield, good quality and filtering and drying characteristics by reacting 2-amino-2-methylbutanenitrile with a metal hypochorite in the presence of water and a mixture of surface active compounds at a temperature of about −10° C. to about 30° C. and recovering the 2,2'-azobis(2-methylbutanenitrile) from the reaction mixture.

5 Claims, No Drawings

PROCESS FOR PREPARING 2,2'-AZOBIS(2-METHYLBUTANENITRILE)

TECHNICAL FIELD

This invention relates to a process for the preparation of 2,2'-azobis(2-methylbutanenitrile) from 2-amino-2-methylbutanenitrile, water, a metal hypochlorite and a mixture of surface active compounds. More specifically, this invention relates to a process for the preparation of 2,2'-azobis(2-methylbutanenitrile) in high yield, good quality and filtering and drying characteristics by reacting an aqueous hypochlorite solution with 2-amino-2-methylbutanenitrile in the presence of a mixture of a surface active quaternary ammonium salt and a surface active nonionic compound.

BACKGROUND ART

Azonitriles are produced by a process described by Anderson in U.S. Pat. No. 2,711,405 which involves reacting the cyanohydrin of an aliphatic ketone with ammonia to form an aminonitrile and oxidatively coupling the aminonitrile to form the azo using an alkali metal or alkaline earth metal hypochlorite in aqueous medium. De Benneville in U.S. Pat. No. 2,713,576 claimed essentially the same process with the addition of alkyl hypochlorites and restriction of aminonitriles to those of acetone, methyl ethyl ketone and diethyl ketone. A process improvement which enables azonitriles to be prepared from aminonitriles of higher molecular weight ketones in good yields is reported by Fuchs in U.S. Pat. No. 3,783,148. Methanol or ethanol is employed as a reaction solvent in proportion to the amounts of aminonitrile and hypochlorite solution used such that, at the completion of the reaction, the alcohol concentration is at least 70% by volume. The alcohol maintains a homogeneous system throughout the reaction and specifically prevents separation of the intermediate, highly hydrophobic chloramines.

U.S. Pat. No. 4,028,345 discloses a process which does not involve the alcohol solvent with all its drawbacks by coupling alpha-aminonitriles in the presence of a metal hypochlorite, water and a surface active compound to form aliphatic azodinitriles.

U.S. Pat. No. 4,051,124 discloses a process for preparing 2,2'-azobis(2-methylpropanenitrile) by coupling 2-amino-2-methylpropanenitrile in the presence of a metal hypochlorite, water and a mixture of a quaternary ammonium compound and a nonionic or amphoteric surface active compound. The 2,2'-azobis (2-methylbutanenitrile) produced by the aforesaid process does not have the quality desired.

DISCLOSURE OF THE INVENTION

It has been found that when 2,2'-azobis (2-methylbutanenitrile) is prepared from 2-amino-2-methylbutanenitrile by reaction with a metal hypochlorite in the presence of water and a mixture of surface active compounds, the 2,2'-azobis(2-methylbutanenitrile) is isolated in high yield and good quality from the reaction mixture by filtration and dried rapidly when one surface active compound is a quaternary ammonium salt of particular chemical structure and the other surface active compound is a nonionic compound of particular chemical structure. Accordingly, the process of the present invention comprises reacting 2-amino-2-methylbutanenitrile with a metal hypochlorite in an aqueous medium in the presence of a mixture of a surface active quaternary ammonium salt and a surface active nonionic compound at a temperature of about $-10°$ C. to about 30° C., the equivalent ratio of metal hypochlorite to aminonitrile being from 1.15:1–1.8:1 and separating the precipitated 2,2'-azobis(2-methylbutanenitrile) from the reaction mixture. This separation is rapidly done by filtration. The azodinitrile thus prepared in high yield, possesses good filtering and drying characteristics and quality.

In the process of this invention, two molecules of the 2-amino-2-methylbutanenitrile are coupled to form the azodinitrile of the present invention. The coupling of the two molecules is accomplished in an aqueous medium with a metal hypochlorite and a mixture of surface active compounds comprising a quaternary ammonium compound and a nonionic compound.

By metal hypochlorite is meant a compound of the formula $M(OCl)_x$ where M is selected from the group consisting of sodium, potassium, calcium and mixtures thereof and x is the valence of M.

The preferred hypochlorite of the present invention, for reasons of convenience and economy, is sodium hypochlorite. Sodium hypochlorite can be prepared by passing chlorine gas into an aqueous sodium hydroxide solution at about 0° C. or it can be purchased commercially. Other hypochlorites can be prepared analogously. For the hypochlorite to be suitable for use in this invention, excess base is used to stabilize the hypochlorite solution. The base may be any water soluble base, preferably sodium or potassium hydroxide, but since sodium hydroxide is normally used in the commercial preparation of sodium hypochlorite, the most preferred base is sodium hydroxide and the amount of excess base must be at least 10 g/l, preferably 15–25 g/l based on one liter of 15% by weight metal hypochlorite. The excess base may, however, be added separately to the reaction mixture or to the hypochlorite. Poor yield or poor quality of the azonitrile may result or an oily product may be obtained if the excess base is not within the above limits. The base levels can be readily controlled by known manufacturing procedures.

The concentration of metal hypochlorite in the aqueous medium initially is from 5–10% by weight, preferably 9%. At hypochlorite concentrations below 5% product yields tend to drop off. Above about 10% hypochlorite concentration, colored product tends to form. When the hypochlorite is calcium hypochlorite, the preferred concentration is reached by dilution with water. Calcium hypochlorite is available as a 100% active material. Sodium hypochlorite is commercially available as a 15% by weight aqueous solution.

The equivalent ratio of metal hypochlorite to the butanenitrile is generally from 1.15:1–1.8:1. Ratios below 1.15:1 will not result in the high yield and good filterability and quality or will not result in product formation. However, ratios above 1.8:1 do result in product formation, but offer no advantage. The aforesaid ratio of 1.15:1–1.8:1 results in high yields. The preferred ratio of the hypochlorite to the butanenitrile is from 1.2:1–1.5:1. The most preferred ratio is 1.3:1. The equivalent ratio referred to herein is defined as the equivalent of metal hypochlorite per mole of aminonitrile. An equivalent of metal hypochlorite is a mole of the hypochlorite divided by the valence of the metal. An equivalent of aminonitrile is the same as the molar amount of aminonitrile.

The 2-amino-2-methylbutanenitrile starting material of the present invention can be obtained from commercial sources or may be prepared by methods well known in the art, for example, by the method described by Knowles in U.S. Pat. No. 3,541,132. A procedure that can be used to obtain the amino compound involves charging 2-butanone to a pressure vessel and cooling this to 5° C. and then adding 1.0% of triethylamine based on the ketone weight. Hydrogen cyanide is then introduced in portions in an amount equimolar to that of the ketone at a temperature between 5° C. and 20° C. The reaction vessel is cooled to about 10° C. and pressurized to 40 psig with ammonia, heated to 50° C. and held at 50° C. and 80 psig for 5 hours and finally cooled and the product is discharged from the vessel.

The use of surface active compounds in the preparation of azodinitrile compounds is disclosed in U.S. Pat. Nos. 4,028,345 and 4,051,124. The disclosure in said U.S. patents is hereby incorporated by reference in the present application. While the function of the surface active compounds in promoting this reaction is unknown, one or both may act as a "catalyst" for the reaction of base (e.g., NaOH) with intermediate formed chloramines and/or may serve as a "solubilizer" for the chloramine and base, or may perform some other function which enables a reaction to occur and a product to be obtained in high yield.

An additional function performed by one of the surface active compounds in the present invention, in particular the nonionic surfactant, is to ensure that impurities that adversely affect quality of the azodinitrile, such as give high color, are not absorbed or adsorbed by the azodinitrile and are free to be removed in the filtrate and wash water.

In addition to promoting efficient reaction and ensuring good quality, the combination of quaternary ammonium and nonionic compounds of types useful in this invention give an azodinitrile with particle physical character which enables rapid filtration and washing to be accomplished.

The quaternary ammonium compounds useful in this invention, their properties and behavior are discussed by Paul Becher in "Emulsions, Theory and Practice", ACS Monograph No. 162, 1965. Although the presence of the quaternary ammonium compounds of the present invention is critical, the amount may vary widely. As little as 0.4 by weight of quaternary ammonium compounds based upon the weight of the butanenitrile can be used. As much as 3.0% can be used. No advantage is realized in using more than 3.0% and a tendency to produce a product with higher color may result at levels of about 3.0%. A preferred range of 0.75-2.0% by weight of quaternary ammonium compounds based on the aminonitrile gives desirable filtration properties. A most preferred level is 1.0%.

The quaternary ammonium compounds of this invention are specifically tetraalkylammonium compounds which fit a specific generic formula. One compound of this type is required, although this does not preclude the use of more than one compound of this type as long as the condition is met that compounds which fit the generic formula are employed.

General formula is

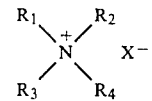

where $R_1$, $R_2$, $R_3$ and $R_4$ are alkyl groups with 1-14 carbon atoms, with at least two alkyl groups having 6-14 carbon atoms. The total number of carbon atoms in $R_1+R_2+R_3+R_4$ ranges from 16-30. The preferred total number of carbon atoms is 18-26 and the preferred quaternary ammonium compounds are those with two alkyl groups of 7-12 carbon atoms and two methyl groups. X is chloride, bromide, hydroxide, acetate, formate or any other anionic group which does not deleteriously affect the performance of the quaternary ammonium cation. The preferred groups are chloride, bromide, hydroxide, acetate and formate.

Representative examples of tetraalkylammonium salts of the formula include:
Dioctyldimethylammonium chloride
Didodecyldimethylammonium chloride
Hexyltetradecyldimethylammonium bromide
Dihexyldiethylammonium acetate
Trioctylmethylammonium bromide For economic and commercial availability reasons the tetraalkylammonium chloride compounds are preferred. Most preferred is dioctyldimethylammonium chloride.

The nonionic surface active compounds useful in this invention fit a specific formula. One compound of this type is required, although this does not preclude the use of more than one compound of this type as long as the condition is met that compounds which fit the generic formula are employed. Compounds of the type useful in this invention are disclosed in McCutcheon's "Detergents & Emulsifiers", North American Edition, 1980 Annual, published by McCutcheon's Division, Mc Publishing Co., Glen Rock, N.J.

General formula is

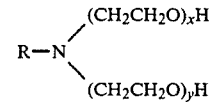

where R is an alkyl group with 8-20 carbon atoms and the total of x and y is 25-65. Most preferred are compounds with $R=14-18$ and $x+y=40-60$.

An additional requirement for the nonionic surface active compound is that it have an HLB number of 16-30, preferably 17-22. Hydrophilic-Lipophilic Balance of a surfactant (HLB) is defined and discussed by Paul Becher in "Emulsions, Theory and Practice", ACS Monograph No. 162, 1965, pages 232-255. The HLB numbers which have been assigned to many surfactants indicate balance in their affinity for water (hydrophilic) or nonpolar organic liquids (lipophilic). A high HLB number indicates high water solubility and low organic solubility, a low number indicates a high organic solubility and low water solubility. Nonionic surfactants useful in this invention have appreciable water solubility.

The amount of nonionic surface active compounds, though critical to the present invention, may vary widely. As little as 0.1% by weight of nonionic compounds based upon the weight of the butanenitrile can be used. As much as 0.75% can be used. No advantage is realized in using more than 0.75% and a tendency toward excessive foaming may result at levels above about 0.75%. A preferred range is 0.15-0.5% by weight of nonionic surfactants based upon the aminonitrile. A most preferred level is 0.33%.

The ratio of weight of quaternary ammonium compound to weight of nonionic compound is also important in this invention. This ratio may be as low as 0.5 and as high as 20. The preferred range of ratios is 2.0-10 and the most preferred ratio is 3.0.

The atmospheric pressure system is entirely aqueous, requiring no organic solvent to be present as a promoter or cosolvent with water in the preferred system. The quaternary ammonium and nonionic surface active compounds are mixed with the water as is the sodium hypochlorite or other metal hypochlorite and the aminonitrile is added with sufficient cooling to handle the heat load. The manner in which the sodium hypochlorite and aminonitrile are combined is a matter of choice. The reactants can be added in separate streams to a body of water containing the surface active compounds or the aminonitrile can be added to an aqueous metal hypochlorite solution containing the surfactants. The latter method is preferred and an addition time of 30-60 minutes is suitable.

The preferred temperature of the present process is 0°-10° C., but temperature may vary beyond our preferred temperature range in the process of the present invention. Desirable yields can be obtained at temperatures as high as 30° C. and as low as −10° C. The process of the present invention can be conducted at temperatures below −10° C. but at such lower temperatures, the danger of freezing of the aqueous mixture becomes greater and reaction times become larger. The use of antifreeze compounds may permit operation of the present process at temperatures lower than −10° C. without freezing. The process of the present invention can also be carried out at temperatures above 30° C. but at higher temperatures the risk of side reactions, azo decomposition and lower product yields, become a serious consideration. Thus, the process of the present invention may be conducted at a temperature that is above the freezing point of the reaction mixture and below the decomposition temperature of the azodinitrile compound.

The time required to complete the reaction of the present invention after the aminonitrile has been added requires about 30 minutes at the preferred temperature.

Following completion of the reaction, the reaction mixture is a slurry of solid product.

The filter time is the time required to remove the liquid in the reaction product slurry leaving a wet cake of product. The wash time is the time required to wash out with water impurities in the wet cake and to remove said water to give a damp cake suitable for drying. The drying time is the time for the damp cake to be dried to constant weight at a set temperature under a constant regulated air flow.

APHA color determinations were by procedure 118 "Color" page 160 (1971) of Standard Methods for Examination of Water and Waste Water.

Control 1

(Quaternary Ammonium Compound of General Formula, No Nonionic Compound)

Sixty grams of 2-amino-2-methylbutanenitrile (AN) of 83.5% purity were added in 60 minutes to a stirred mixture of 552 g 9% sodium hypochlorite solution containing 15 g of NaOH per liter of hypochlorite (15% basis) and 0.6 g dioctyldimethylammonium chloride (1% of AN weight). The mixture was maintained at 0° C. during the addition. The equivalent ratio of NaOCl-to-AN was 1.3:1. The reaction mixture was stirred for 30 minutes longer at 0° C. and filtered. Filtration was conducted through 12.5 cm Whatman #41 paper on a Büchner funnel under 23 cm (9 in) Hg vacuum. The cake was washed with a volume of water equal to twice the volume of the reaction mixture. A soft, tacky, yellow solid product was obtained and was not dried, but was discarded.

Control 2

(Nonionic Compound of General Formula, No Quaternary Ammonium Compound)

Following the procedure of Control 1, 0.2 g of a nonionic surfactant (0.33% of AN weight) was used in place of the dioctyldimethylammonium chloride. The nonionic compound fit the general formula

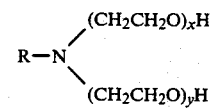

where R=a fatty alkyl group with 18 carbon atoms, $x+y=50$ and had an HLB number of 17.8. A viscous yellow oil formed during the addition of the 2-amino-2-methylbutanenitrile and the preparation was discontinued.

BEST MODE

Example 1

(Combination of Most Preferred Surface Active Quaternary Ammonium Salt and Nonionic Compound)

Following the procedure of Control 1, a combination of 0.6 g dioctyldimethylammonium chloride (1% of AN weight) and 0.20 g of the nonionic compound used in Control 2 (0.33% of AN weight) was employed in place of the individual surface active compounds. The weight ratio of the surfactants was 3.0. The slurry of solid product was filtered and washed in 1 minute and 35 seconds, a very desirable rapid time. The white cake was dried in a forced air oven for 30 minutes at 40° C. The dry 2,2'-azobis(2-methylbutanenitrile) weighed 47.1 g, a 96% yield. The APHA color of the azodinitrile was determined as 10, well below the maximum of 20 allowable for most polymer production.

Control 3

(Combination of Quaternary Ammonium Salt of the General Formula and Nonionic Compound Not of the General Formula)

Following the procedure of Control 1, 0.6 g dioctyldimethylammonium chloride (1% of AN weight) and 0.2 g of a nonionic surfactant, a polyoxyethylene glycol monostearate with an HLB number of 16.8, 0.33% of AN weight, were combined. The slurry of solid product was filtered and washed in 1 minute and 50 seconds. The cake was dried in a forced air oven for 30 minutes at 40° C. The dry 2,2'-azobis(2-methylbutanenitrile) weighed 45.8 g, a 93.3% yield. The APHA color of the azodinitrile was found to be 30, unacceptably high for commercial use.

Control 4

(Combination of Nonionic Compound of the General Formula and Quaternary Ammonium Salt Not of the General Formula)

Following the procedure of Control 1, 0.6 g hexadecyltrimethylammonium chloride (1% of AN weight) and 0.2 g of a nonionic compound (0.33% of AN weight) which fits the general formula

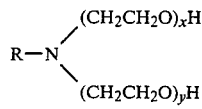

where R=a fatty alkyl group with 18 carbon atoms, x+y=50 and had an HLB number of 17.8 were combined for use in this preparation. The slurry of solid product was filtered and washed in 4 minutes 25 seconds, much slower than acceptable. The cake was dried in a forced air oven for 30 minutes at 40° C. The dry 2,2′-azobis (2-methylbutanenitrile) weighed 43.8 g, an 89.2% yield, less than attainable by the Best Mode of Example 3. The APHA color was 10.

Control 5

(Combination of Quaternary Ammonium Salt and Nonionic Compound, Neither Compound is of the General Formula)

Following the procedure of Control 1, 0.6 g hexadecyltrimethylammonium chloride (1% of AN weight) and 0.2 g of a polyoxyethylene glycol monolauryl ether with an HLB number of 17.0 (0.33% of AN weight) were combined for this preparation. The slurry of solid product was filtered and washed in 6 minutes, slower than acceptable. The cake was dried in a forced air oven for 30 minutes at 40° C. The dry 2,2′-azobis(2-methylbutanenitrile) weighed 42.8 g, an 87.2% yield, less than attainable by the Best Mode of Example 3. The APHA color was 10.

Example 2

One hundred twenty grams of 2-amino-2-methyl-butanenitrile (AM) of 84% purity were added in 45 minutes to a stirred mixture of 1275 g 9% sodium hypochlorite solution containing 25 g of NaOH per liter of hypochlorite solution (15% basis), 2.4 g dihexyldiethylammonium acetate (2% of AN weight) and 0.6 g of nonionic compound of structure

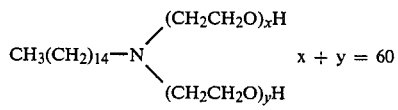

(0.5% of AN weight) which has an HLB no. 20. The weight ratio of ammonium salt and nonionic compound was 4.0. The reaction mixture was maintained at 10° C. during the addition period and for 30 minutes afterward. The equivalent ratio of NaOCl-to-AN was 1.5:1. The mixture was filtered and washed in 1 minute and 40 seconds as in Example 1 and the cake was dried at 40° C. Weight was 94.3 g, a 95.5% yield. APHA color was 7.

Examples 3–5

Example 1 is repeated with the exception that the following quaternary ammonium salts are used in place of dioctyldimethylammonium chloride:

|  | Filter & Wash Time | Yield (%) | Color (APHA) |
| --- | --- | --- | --- |
| Ex. 3 | Didodecyldimethylammonium chloride | | |
|  | 1 min. 30 sec. | 94.6 | 5 |
| Ex. 4 | Hexyltetradecyldimethylammonium bromide | | |
|  | 1 min. 45 sec. | 95 | 15 |
| Ex. 5 | Trioctylmethylammonium chloride | | |
|  | 1 min. 50 sec. | 93.5 | 8 |

Examples 6 and 7

Example 1 is repeated with the following amounts and ratios of quaternary ammonium salt and nonionic surfactant:

|  | Wt Ammon. Salt(s) | Wt Nonionic Compound(s) | Ratio Ammon./Nonionic |
| --- | --- | --- | --- |
| Ex. 6 | 1.2 | 0.12 | 10 |
| Ex. 7 | 1.08 | 0.156 | 6.9 |

|  | Filter & Wash Time | Yield (%) | Color (APHA) |
| --- | --- | --- | --- |
| Ex. 6 | 2 min. | 95 | 15 |
| Ex. 7 | 1 min. 20 sec. | 92.5 | 10 |

INDUSTRIAL APPLICABILITY

The azodinitrile compound produced by the process of this invention can be used as a polymerization initiator in emulsion dispersion and solution systems. Polymerizations involving vinyl chloride, methyl methacrylate and butadiene-styrene are merely examples of such systems in industry that would benefit from the use of such initiators.

I claim:

1. A process for the preparation of 2,2′-azobis(2-methylbutanenitrile) comprising:
   (a) reacting at a temperature of from −10° C. to 30° C.;
      (i) 2-amino-2-methylbutanenitrile;
      (ii) a 5 to 10% by weight aqueous metal hypochlorite solution having at least 10 g excess base per liter;
      (iii) at least 0.4% by weight based on the butanenitrile of a quaternary ammonium compound of the formula:

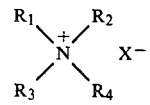

wherein $R_1$, $R_2$, $R_3$ and $R_4$ are alkyl groups with 1–14 carbon atoms, with at least two alkyl groups having 6–14 carbon atoms with the total number of carbon atoms in $R_1+R_2+R_3+R_4$ from 16 to 30 and X is chloride bromide, hydroxide, acetate, formate or any other anionic group which does not deleteriously affect the performance of the quaternary ammonium cation, and at least 0.1% by weight based on the butanenitrile of a nonionic compound of the formula:

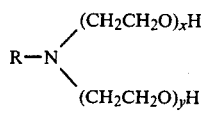

wherein R is an alkyl group with 8–20 carbon atoms, $x+y=25-65$ and $HLB=16-30$; the equivalent ratio of (ii) to (i) being from 1.15:1–1.8:1 and the ratio of the weight of the quaternary ammonium compound to the weight of nonionic compound being from 0.5:1 to 20:1;

(b) recovering the 2,2'-azobis(2-methylbutanenitrile) produced.

2. A process for the preparation of 2,2'-azobis(2-methylbutanenitrile) comprising:

(a) reacting at a temperature of from $-10°$ C. to $30°$ C.;

(i) 2-amino-2-methylbutanenitrile;

(ii) a 9% by weight aqueous solution of sodium, potassium, or calcium hypochlorite, or mixtures thereof, having at least 15–25 g excess base per liter;

(iii) at least 0.75–2.0% by weight, based on the butanenitrile, of a quaternary ammonium compound of the formula:

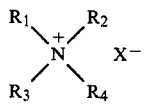

wherein $R_1$, $R_2$, $R_3$ and $R_4$ are alkyl groups with 1–14 carbon atoms, with at least two alkyl groups having 7–12 carbon atoms and two methyl groups with the total number of carbon atoms in $R_1+R_2+R_3+R_4$ from 18 to 26 and X is chloride, bromide, hydroxide, acetate or formate, and at least 0.15–0.5% by weight based on the butanenitrile of a nonionic compound of the formula:

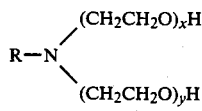

wherein R is an alkyl group with 14–18 carbon atoms, $x+y=40-60$ and $HLB=17-22$; the equivalent ratio of (ii) to (i) being from 1.2:1–1.5:1 and the ratio of the weight of the quaternary ammonium compound to the weight of nonionic compound being from 2.0:1 to 10:1;

(b) recovering the 2,2'-azobis(2-methylbutanenitrile) produced.

3. A process for the preparation of 2,2'-azobis(2-methylbutanenitrile) comprising:

(a) reacting at a temperature of from 0° to 10° C.

(i) 2-amino-2-methylbutanenitrile;

(ii) a 9% by weight aqueous sodium hypochlorite solution having at least 15–25 g excess base per liter;

(iii) at least 1% by weight based on the butanenitrile of a quaternary ammonium compound of the formula:

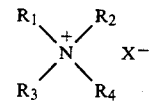

wherein $R_1$, $R_2$, $R_3$ and $R_4$ are alkyl groups with 1–14 carbon atoms, with at least two alkyl groups having 7–12 carbon atoms and two methyl groups with the total number of carbon atoms in $R_1+R_2+R_3+R_4$ from 18 to 26 and X is chloride, bromide, hydroxide, acetate or formate, and at least 0.33% by weight based on the butanenitrile of a nonionic compound of the formula:

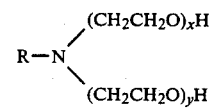

where R is an alkyl group with 14–18 carbon atoms, $x+y=40-60$ and $HLB=17-22$; equivalent ratio of (ii) to (i) being 1.3:1 and the ratio of the weight of the quaternary ammonium compound to the weight of nonionic compound is 3.0:1;

(b) recovering the 2,2'-azobis(2-methylbutanenitrile) produced.

4. The process of claim 3 wherein the quaternary ammonium compound is a tetraalkylammonium chloride compound.

5. The process of claim 3 wherein the quaternary ammonium compound is dioctyldimethylammonium chloride and the nonionic compound is of the formula:

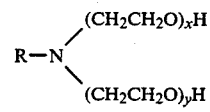

where R is an alkyl group with 18 carbon atoms, $x+y=50$ and $HLB=17.8$.

* * * * *